(12) United States Patent
Taylor et al.

(10) Patent No.: US 10,388,029 B1
(45) Date of Patent: Aug. 20, 2019

(54) MULTI-SENSOR POSE-ESTIMATE SYSTEM

(71) Applicants: Joseph Taylor, San Jose, CA (US); Ryan K. Hashimoto, Hawthorne, CA (US)

(72) Inventors: Joseph Taylor, San Jose, CA (US); Ryan K. Hashimoto, Hawthorne, CA (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 68 days.

(21) Appl. No.: 15/698,353

(22) Filed: Sep. 7, 2017

(51) Int. Cl.
| | |
|---|---|
| *G06T 7/00* | (2017.01) |
| *G06T 7/73* | (2017.01) |
| *G01N 21/88* | (2006.01) |
| *G01S 17/89* | (2006.01) |
| *G06K 9/00* | (2006.01) |
| *G01N 21/17* | (2006.01) |

(52) U.S. Cl.
CPC .......... *G06T 7/75* (2017.01); *G01N 21/8851* (2013.01); *G01S 17/89* (2013.01); *G06K 9/00214* (2013.01); *G06T 7/0006* (2013.01); *G06T 7/97* (2017.01); *G01N 2021/177* (2013.01); *G06T 2207/30244* (2013.01)

(58) Field of Classification Search
CPC ................. G06T 7/75; G06T 7/97; G06T 7/0006; G06T 2207/30244; G01N 21/8851; G01N 2021/177; G01S 17/89; G06K 9/00214
See application file for complete search history.

(56) References Cited

U.S. PATENT DOCUMENTS

| | | | |
|---|---|---|---|
| 2011/0157178 A1* | 6/2011 | Tuzel | G06T 1/00 345/426 |
| 2013/0070108 A1* | 3/2013 | Aerts | F01D 21/003 348/187 |
| 2016/0012643 A1* | 1/2016 | Kezele | G06T 19/006 345/633 |
| 2018/0249144 A1* | 8/2018 | Feng | G06T 7/579 |

\* cited by examiner

*Primary Examiner* — Zhihan Zhou
(74) *Attorney, Agent, or Firm* — Tarolli, Sundheim, Covell & Tummino LLP

(57) ABSTRACT

One example includes a pose-estimate system. The system includes a vision system that includes a plurality of image sensors. Each of the plurality of image sensors captures an image with respect to a respective image plane. At least one of the respective images includes a feature of a target object. The system also includes a pose-estimation processor that aggregates the images corresponding to the respective image planes onto a virtual image plane to generate a pose estimate of the feature of the target object in three-dimensional space.

15 Claims, 3 Drawing Sheets

MULTI-SENSOR POSE-ESTIMATE SYSTEM

GOVERNMENT INTEREST

The invention was made under Government Contract Number FA8650-04-2-3450. Therefore, the US Government has rights to the invention as specified in that contract.

TECHNICAL FIELD

This disclosure relates generally to sensor systems, and specifically to a multi-sensor pose-estimate system.

BACKGROUND

Pose-estimation relates to the ability to relate an object in three-dimensional space to two-dimensional imagery of the object. Pose-estimation, or "Perspective-n-Point", is typically formulated as the determination of the rigid transformation between an object image and some known three-dimensional configuration of features on the target object. As an example, a set of image coordinates [u,v] corresponding to known features on the object of interest are input to an algorithm. For example, the image coordinates of the target object can be collected from a camera in the form of a video stream, or a set of images, where feature coordinates in individual frames are obtained through some automated feature detection process. The image points can then be used in the pose-estimation function along with the three-dimensional position of the features defined in the object space to determine a relative position and orientation between the camera and the target object.

SUMMARY

One example includes a pose-estimate system. The system includes a vision system that includes a plurality of image sensors. Each of the plurality of image sensors captures an image with respect to a respective image plane. At least one of the respective images includes a feature of a target object. The system also includes a pose-estimation processor that aggregates the images corresponding to the respective image planes onto a virtual image plane to generate a pose estimate of the feature of the target object in three-dimensional space.

Another example includes a computer readable medium that is configured, when executed, to implement a method for generating a pose-estimate of a feature of a target object. The method includes capturing a plurality of images via a vision system comprising a respective plurality of image sensors. Each of the images can be associated with a respective image plane. The image associated with at least one of a respective one of the plurality of image sensors includes the feature of the target object. The method also includes providing image data associated with the plurality of images to a pose-estimation processor. The method also includes implementing a pose-estimation algorithm via the pose-estimation processor to calculate a plurality of translation vectors from the vision system to a set of feature points associated with the feature of the target object with respect to a virtual image plane comprising the image data corresponding to the image plane associated with each of the plurality of image sensors. The method further includes generating the pose-estimate of the feature of the target object in three-dimensional space based on the plurality of translation vectors associated with the virtual image plane.

Another example includes a pose-estimate system. The system includes a vision system comprising a plurality of image sensors. Each of the plurality of image sensors captures an image with respect to a respective image plane, at least one of the respective images comprising a feature of a target object. The image planes can be at least partially non-overlapping with respect to each other. The system also includes a pose-estimation processor that implements a pose-estimation algorithm to aggregate the images corresponding to the respective image planes onto a virtual image plane based on predetermined baseline spatial and orientation data associated with each of the plurality of image sensors with respect to each other, to calculate a plurality of translation vectors from the vision system to a set of feature points associated with the feature of the target object with respect to the virtual image plane, and to generate a pose estimate of the feature of the target object in three-dimensional space based on the plurality of translation vectors.

DETAILED DESCRIPTION

This disclosure relates generally to sensor systems, and specifically to a multi-sensor pose-estimate system. The multi-sensor pose-estimation system can be implemented in any of a variety of systems or applications that can require visualization of three-dimensional aspects of a target object based on two-dimensional image data. For example, the multi-sensor pose-estimation system can be implemented in autonomous vehicle control systems, or can be used for aerial refueling of an aircraft.

The multi-sensor pose-estimation system includes a vision system that includes a plurality of image sensors (e.g., cameras) that are configured to capture images of the target object. As an example, the image sensors can each have an associated image plane that can be at least partially non-overlapping with respect to the image planes of the respective other image sensors. Thus, one of the image sensors can capture an image of a feature of the target object, such that a pose estimate of the target object can be generated, with the feature of the target object being three-dimensionally visualized with respect to the target object. The vision system can provide image data to a pose-estimation processor. The pose-estimation processor is configured to implement a pose-estimation algorithm that is configured to aggregate the image data associated with each of the image sensors into a composite virtual image plane.

As an example, the pose-estimation algorithm can be configured to implement a least squares summation function to substantially minimize an error vector between an actual location of the feature in three-dimensional space and a perceived location in three-dimensional space. The pose-estimation algorithm can incorporate predetermined baseline spatial and orientation data of the image sensors with respect to each other. The least squares summation function can include, for example a number of least square summation equation sets corresponding to a number of image sensors, such that each equation can correspond to a first image plane associated with a first image sensor relative to another image plane of a respective other image sensor. Thus, the pose-estimation algorithm can spatially incorporate the image plane associated with each other one of the plurality of image sensors into the first image plane to generate the virtual image plane. For example, the pose-estimation algorithm can then generate the pose-estimate based on determining translation vectors from the focal point of the first image sensor to the feature based on the least squares summation equation sets.

Figure 1:
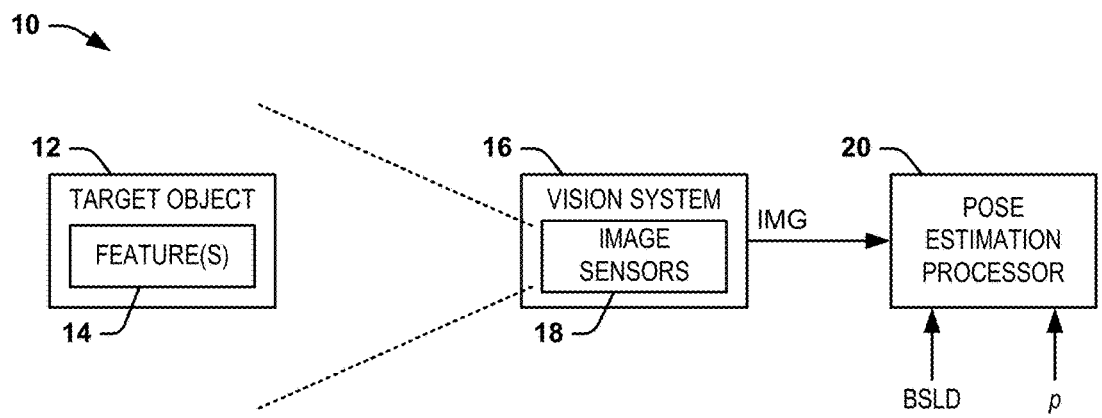
FIG. 1 illustrates an example of a pose-estimate system.

FIG. 1 illustrates an example of a pose-estimate system 10. The pose-estimation system 10 can be implemented in any of a variety of systems or applications that can require visualization of three-dimensional aspects of a target object 12 based on two-dimensional image data. For example, the pose-estimation system can be implemented in autonomous vehicle control systems, or can be used for aerial refueling of an aircraft. Thus, the pose-estimation system 10 can be configured to generate a pose-estimate of the target object 12, as well as three-dimensional data of one or more features 14 of the target object 12.

The pose-estimation system 10 includes a vision system 16 that is configured to generate image data IMG. The vision system 16 includes a plurality of image sensors (e.g., cameras) 18 that are each configured to capture respective images (e.g., sequential image frames) that each may include the target object 12. Each of the image sensors 18 can have an associated image plane associated with the captured images of the respective image sensor 16. Thus, the image data IMG can correspond to data associated with the images captured by each of the image sensors 18, and can thus correspond to images concurrently captured by each of the respective image sensors 18 that are provided as sequential image frames in a video stream. The vision system 16 can implement any arrangement of the image sensors 18, such that the image sensors 18 are not limited to any given placement or orientation restrictions. While the image sensors 18 are described herein as cameras, it is to be understood that other types of image sensors can be used in the pose-estimation system 10, such as radar, lidar, or other types of image-capturing sensors.

The pose-estimation system 10 also includes a pose-estimate processor 20 that is configured to implement a pose-estimation algorithm to generate the pose-estimate based on the image data IMG and based on predetermined baseline spatial and orientation data associated with the image sensors 18, demonstrated in the example of FIG. 1 as a signal BSLD. In addition, in the example of FIG. 1, the pose-estimation processor 20 is demonstrated as receiving a set of predetermined target object features p. As an example, the set of predetermined target object features p can represent target object feature points, and/or can include feature point collinearity vector geometry data.

As described in greater detail herein, the pose-estimation algorithm can be configured to implement a least squares summation function to substantially minimize an error vector between an actual location of the feature(s) 14 in three-dimensional space and a perceived location of the feature(s) 14 in three-dimensional space based on the predetermined baseline spatial and orientation data BSLD and based on the set of predetermined target object features p. The least squares summation function can include, for example a number of least square summation equation sets corresponding to a number of image sensors, such that each equation can correspond to a first image plane associated with a given one image sensor 18 relative to another image plane of a respective other one of the image sensors 18. Thus, the pose-estimation algorithm can spatially incorporate the image plane associated with each other one of the image sensors 18 into the first image plane to generate the virtual image plane. For example, the pose-estimation algorithm can then generate the pose-estimate based on determining translation vectors from the focal point of the first image sensor 18 to the feature based on the least squares summation equation sets.

Thus, as described herein, the pose-estimate processor 20 generates the pose-estimate of the target object 12 from any number of image sensors 18 in a manner that does not rely on the use of stereo vision of the image sensors 18. Furthermore, as also described herein, the pose-estimate generated by the pose-estimation processor 20 is void of any errors associated with baseline length, as described in greater detail herein.

Figure 2:
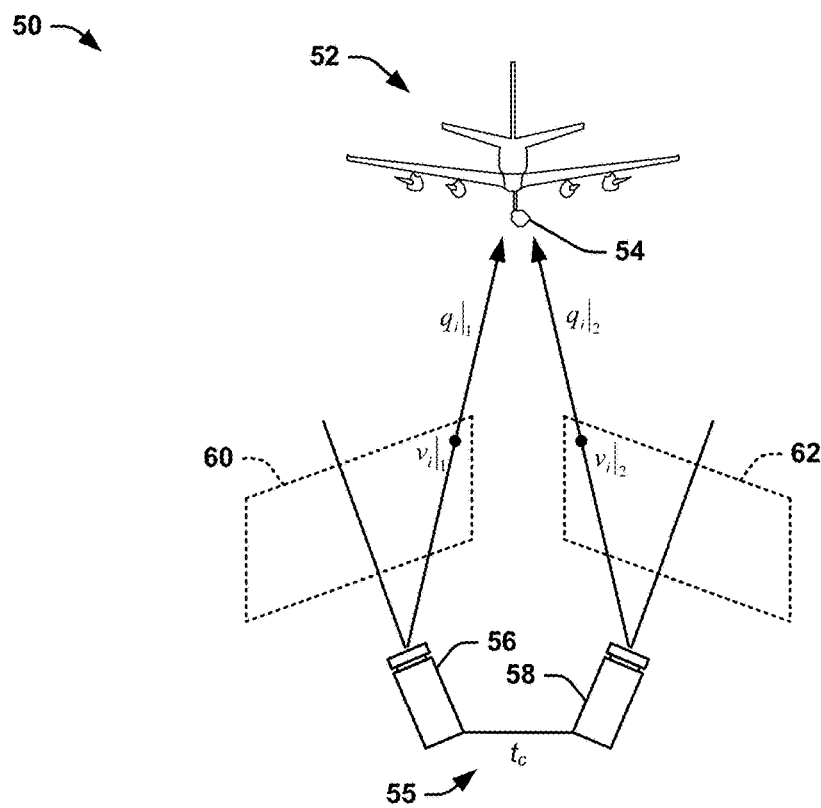
FIG. 2 illustrates an example diagram of a pose-estimate system.

FIG. 2 illustrates an example diagram 50 of a pose-estimate system. The diagram 50 can demonstrate another example of the pose-estimate system 10 in the example of FIG. 1. Therefore, reference is to be made to the example of FIG. 1 in the following description of the example of FIG. 2. In the example of FIG. 2, the diagram 50 demonstrates generating a pose-estimate of an aircraft 52 corresponding to a target object 12, such as including a refueling hose and drogue 54 that can correspond to a feature 14, during an aerial refueling.

The diagram 50 demonstrates a vision system 55 that includes a first camera 56 and a second camera 58. The first camera 56 is configured to capture an image with respect to a first image plane 60 corresponding to a field of view of the first camera 56, and the second camera 58 is configured to capture an image with respect to a second image plane 62 corresponding to a field of view of the second camera 58. The images concurrently captured by the first and second cameras 56 and 58 can correspond to the image data IMG. In the example of FIG. 2, the first and second image planes 60 and 62 are demonstrated as at least partially non-overlapping, such that portions of the first or second image on the respective first and second image planes 60 and 62 is not shared between the first and second image planes 60 and 62. The vision system 55 is demonstrated as being oriented such that first camera 56 and the second camera 58 have a direction cosine matrix $R_c$ with respect to each other and have a translation vector $t_c$, and also have image-space feature points of $v_i|_1$ and $v_i|_1$, respectively, that can correspond to two-dimensional pixel locations with respect to the respective first and second image planes 60 and 62. The diagram 50 also demonstrates a set of feature points $q_i|_1$ and $q_i|_2$, respectively, associated with the first and second cameras 56 and 58, respectively, of the aircraft 52 from respective focal points, as perceived by the respective cameras 56 and 58.

Figure 3:
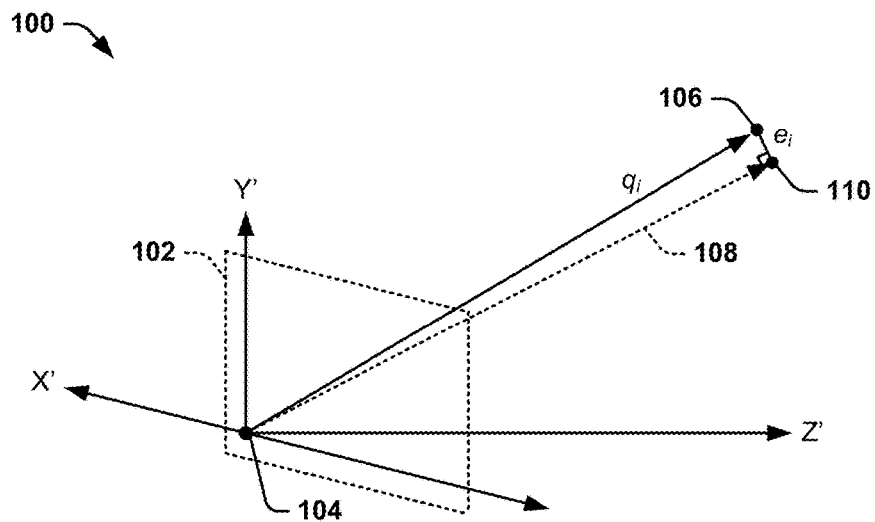
FIG. 3 illustrates an example diagram of pose-estimation relative to an image plane.

FIG. 3 illustrates an example diagram 100 of pose-estimation relative to an image plane 102. The image plane 102 in the diagram 100 can correspond to one of the image planes 60 and 62. In the example of FIG. 3, the image plane 102 is demonstrated as a camera-fixed image plane that is centered about and forward of a focal point 104 of the respective camera, with the focal point 104 being demonstrated at an origin of a coordinate frame defined by a camera frame X', Y', and Z'. Therefore reference is to be made to the example of FIGS. 1 and 2 in the following description of the example of FIG. 3.

The diagram 100 includes a first vector $q_i$ that corresponds to a projection vector from the focal point 104 to an actual feature point 106. The diagram 100 also demonstrates a vector 108 from the focal point 104 to a feature point 110 that can correspond to a perceived feature point on the target object 12 (e.g., the aircraft 52). The feature point 110 can correspond to a perceived location of the actual feature point 106, as perceived by the respective image sensor (e.g., one of the first and second cameras 56 and 58). Thus, the diagram 100 further demonstrates an error vector $e_i$ between the vector $q_i$ and the vector 108 corresponding to a difference in three-dimensional space between the actual feature point 106 and the perceived feature point 110.

In the examples of FIGS. 2 and 3, to generate the pose-estimate, the pose-estimation algorithm evaluates the image data from both of the first and second cameras 56 and 58. Since the transformation between the first and second cameras 56 and 58 is a predetermined parameter obtained through extrinsic calibration, the first camera 56 is selected for the following description of generating the pose-estimate. Based on the predetermined baseline spatial and orientation definitions of the first and second cameras 56 and 58, the following relationships directly follow:

$$R_1 = R_c \cdot R_2 \rightarrow R_2 = R_c^T \cdot R_1 \qquad \text{Equation 1}$$

$$t_2 = R_c^T \cdot (t_1 + t_c) \qquad \text{Equation 2}$$

Where, $R_1$ and $R_2$ represent the respective rotations from the object frame to a first camera frame and to a second camera frame, respectively. Similarly, $t_1$ and $t_2$ represent the translation vectors from the first camera frame to the object frame, defined in the first and second camera frames, respectively. Thus, as described herein, the pose-estimate algorithm is configured to aggregate the image data IMG with respect to the first camera frame that can correspond to a single virtual image plane. Applying the relationships of the translation vectors $t_1$ and $t_2$, the feature points of the second camera 62, $q_i|_2$, can now be described in terms of object frame features, $p_i$, as:

$$q_1|_2 = R_2 \cdot p_i + t_2 \rightarrow q_1|_2 = R_c^T \cdot R_1 \cdot p_i + R_c^T \cdot (t_1 + t_c) \qquad \text{Equation 3}$$

The calculation of the feature points $q_i|_2$ can be implemented to restructure the pose-estimate. Additionally, the object-space collinearity error vector $e_i$ can be expressed as:

$$e_i = (I - \hat{V}_i)(R \cdot p_i + t) \qquad \text{Equation 4}$$

The quantity $\hat{V}_i$ in Equation 4 refers to the observed line-of-sight projection matrix defined as:

$$\hat{V}_i = \frac{v_i \cdot v_i^T}{v_i^T \cdot v_i} \qquad \text{Equation 5}$$

Where $v_i$ is the $i^{th}$ image-space feature point. Because $\hat{V}_i$ is a projection operator, the following properties apply:

$$\hat{V}_i^T = \hat{V}_i, \qquad \text{Equation 6a}$$

$$\hat{V}_i^2 = \hat{V}_i \cdot \hat{V}_i^T = \hat{V}_i, \qquad \text{Equation 6b}$$

$$(\hat{V}_i - I)^T \cdot (\hat{V}_i - I) = (I - \hat{V}_i)^T \cdot (I - \hat{V}_i) = I - \hat{V}_i. \qquad \text{Equation 6c}$$

Note that the projection operator $\hat{V}_i$ applies to all feature points, regardless of the image plane in which they reside.

As described hereafter, A defines the set of all feature points visible in the first camera 60 and B defines the set of all feature points visible in the second camera 62, and n defines the number of cameras. The minimization of the sum of the squared object-space collinearity errors in Equation 4 is expressed as:

$$\sum_{i=1}^{n} \|e_i\|^2 = \sum_{i=1}^{n} \|(I - \hat{V}_i)(R \cdot p_i + t)\|^2 = \qquad \text{Equation 7}$$

$$\sum_{i \in A,B} \|(I - \hat{V}_i)(R_c^T \cdot R_1 \cdot p_i + R_c^T \cdot t_1 + R_c^T \cdot t_c)\|^2$$

Where:

$$R_c = I, \; t_c = 0 \text{ when } p_i \in A \qquad \text{Equation 8}$$

Equation 7 thus defines a sum of the squared object-space collinearity errors corresponding to the first camera 56 relative to the second camera 58 and the first camera 56 with respect to itself. Thus, the sum of the squared object-space collinearity errors provided by Equation 7 reduces the error vector $e_i$ of the first image plane 60 corresponding to the virtual image plane with respect to the feature points of the second image plane 62. As an example, for a pose-estimation system 10 that includes a third camera, another sum of the squared object-space collinearity errors would be calculated for the first camera 60 relative to a third camera (e.g., with a variable C defining the set of all feature points visible in the third camera).

Given some fixed $R_1$, an optimal value of the translation vector $t_1$ can now be calculated. As an example, the pose-estimation algorithm can provide an initial estimate for $R_1$. However, such an initial estimate can be readily assumed for many applications. For example, determination of an initial estimate for the aerial refueling application can be surmised where the approximate refueling geometry between two aircraft is a priori known. Therefore, given the initial estimate of $R_1$, Equation 7 is regrouped as follows:

$$\sum_{i \in A,B} \left\| \underbrace{(I - \hat{V}_i)(R_c^T)(R_1 \cdot p_i + t_c)}_{-b_i} + \underbrace{(I - \hat{V}_i)(R_c^T)}_{A_i} \cdot t_1 \right\|^2 \qquad \text{Equation 9}$$

The optimal $t_1$ value can now be obtained by solving the expression:

$$\sum_i A_i^T \cdot A_i \cdot t_1 - A_i^T \cdot b_i = 0 \rightarrow t_1 = \left( \sum_i A_i^T A_i \right)^{-1} \cdot \left( \sum_i A_i^T b_i \right) \qquad \text{Equation 10}$$

Substituting $A_i$ and $b_i$ into Equation 10 and using the projection operator properties defined in Equation 6 to reduce, the following result is obtained:

$$\sum_i A_i^T A_i \qquad \text{Equation 11}$$

$$\sum_i \left[ (I - \hat{V}_i)(R_c^T) \right]^T \left[ (I - \hat{V}_i)(R_c^T) \right]$$

$$\sum_i (R_c)(I - \hat{V}_i)^T (I - \hat{V}_i)(R_c^T)$$

$$\sum_i R_c \cdot (I - \hat{V}_i) \cdot R_c^T$$

-continued

AND $$\sum_i A_i^T b_i \qquad \text{Equation 12}$$

$$\sum_i \left[(I - \hat{V}_i)(R_c^T)\right]^T (I - \hat{V}_i)(-R_c^T)(R_1 \cdot p_i + t_c)$$

$$\sum_i R_c \cdot (I - \hat{V}_i)^T (I - \hat{V}_i)(-R_c^T)(R_1 \cdot p_i + t_c)$$

$$\sum_i R_c \cdot (I - \hat{V}_i)(-R_c^T)(R_1 \cdot p_i + t_c)$$

$$\sum_i R_c \cdot (\hat{V}_i - I)(R_c^T)(R_1 \cdot p_i + t_c)$$

Thus, the optimal value of the translation vector $t_1$ is:

$$t_1(R_1) = \qquad \text{Equation 13}$$

$$\left(\sum_i R_c \cdot (I - \hat{V}_i) \cdot R_c^T\right)^{-1} \cdot \sum_i R_c \cdot (\hat{V}_i - I)(R_c^T)(R_1 \cdot p_i + t_c)$$

Refined values of the $R_1$ and $t_1$ can be computed iteratively. As an example, the feature points of the first camera frame can be defined in terms of the second camera frame. The pose-estimation algorithm can implement the previous definition of $q_1|_2$, from Equation 3:

$$q_i|_2 = R_c^T \cdot R_1 \cdot p_i + R_c^T \cdot (t_1 + t_c) = R_c^T \cdot (R_1 \cdot p_i + t_1 + t_c) = \qquad \text{Equation 14}$$
$$R_c^T \cdot (q_i|_1 + t_c) \Rightarrow q_i|_1 = R_c \cdot q_i|_2 - t_c$$

The pose-estimation algorithm then calculates the rotation from the object frame to the first camera frame as follows:

$$R_1^{(K+1)} = \arg\min_{R_1} \left[ \sum_{i \in A} \left\| R_1^{(k)} \cdot p_i + t_1^{(k)} - \hat{V}_i \cdot q_i^{(k)} \right\|_1^2 + \sum_{i \in B} \left\| R_1^{(k)} \cdot p_i + t_1^{(k)} - \hat{V}_i \cdot q_i^{(k)} \right\|_1^2 \right] \qquad \text{Equation 15}$$

As an example, Equation 14 can be expressed as follows, based on the pose-estimation system 10 including an arbitrary number of cameras, where set Z represents feature points viewed by camera n:

$$R_1^{(K+1)} = \arg\min_{R_1} \left[ \sum_{i \in A} \left\| R_1^{(k)} \cdot p_i + t_1^{(k)} - \hat{V}_i \cdot q_i^{(k)} \right\|_1^2 + \sum_{i \in B} \left\| R_1^{(k)} \cdot p_i + t_1^{(k)} - \hat{V}_i \cdot q_i^{(k)} \right\|_1^2 + \ldots + \sum_{i \in Z} \left\| R_1^{(k)} \cdot p_i + t_1^{(k)} - \hat{V}_i \cdot q_i^{(k)} \right\|_1^2 \right] \qquad \text{Equation 16}$$

Where: $R_c = R_{CAM2 \text{ to } CAM1}$, $t_c = t_{CAM2 \text{ to } CAM1}|_1$
when $p_i \in B$
$\vdots$
$R_c = R_{CAMn \text{ to } CAM1}$, $t_c = t_{CAMn \text{ to } CAM1}|_1$ when $p_i \in Z$ Implementing Equation 15, in the example of FIG. 2 implementing the dual cameras of the first and second cameras 56 and 58, is equivalent to:

$$R_1^{(K+1)} = \arg\max_{R_1} tr(R_1^{T(k)} \cdot M(R_1^{(k)})) \qquad \text{Equation 17}$$

Where:

$$M(R) = \sum_{i \in A} q_i'(R) \cdot p_i'^T + \sum_{i \in B} q_i'(R) \cdot p_i'^T \qquad \text{Equation 18}$$

And where:

$$p_i' = p_i - \bar{p}, \; q_i'(R) = q_i(R) - \bar{q}(R) \qquad \text{Equation 19}$$

In Equation 19, the mean values of p and q are computed over all i∈A, B. The rotation from the object frame to the first camera frame, $R_1^{(K+1)}$, follows directly through use of the singular value decomposition (SVD) of M, (U, Σ, V):

$$R_1^{(K+1)} = V \cdot U^T \qquad \text{Equation 20}$$

The iterative process is completed by an update to the translation vector $t_1$:

$$t_1^{(k+1)} = t_1(R^{(k+1)}) \qquad \text{Equation 21}$$

The updates to the translation vectors $t_1$ are repeated by the pose-estimation algorithm until a predetermined (e.g., programmably specified) convergence tolerance level is reached, at which point the pose-estimation processor 20 terminates the pose-estimation algorithm to obtain a pose-estimate.

Figure 4:
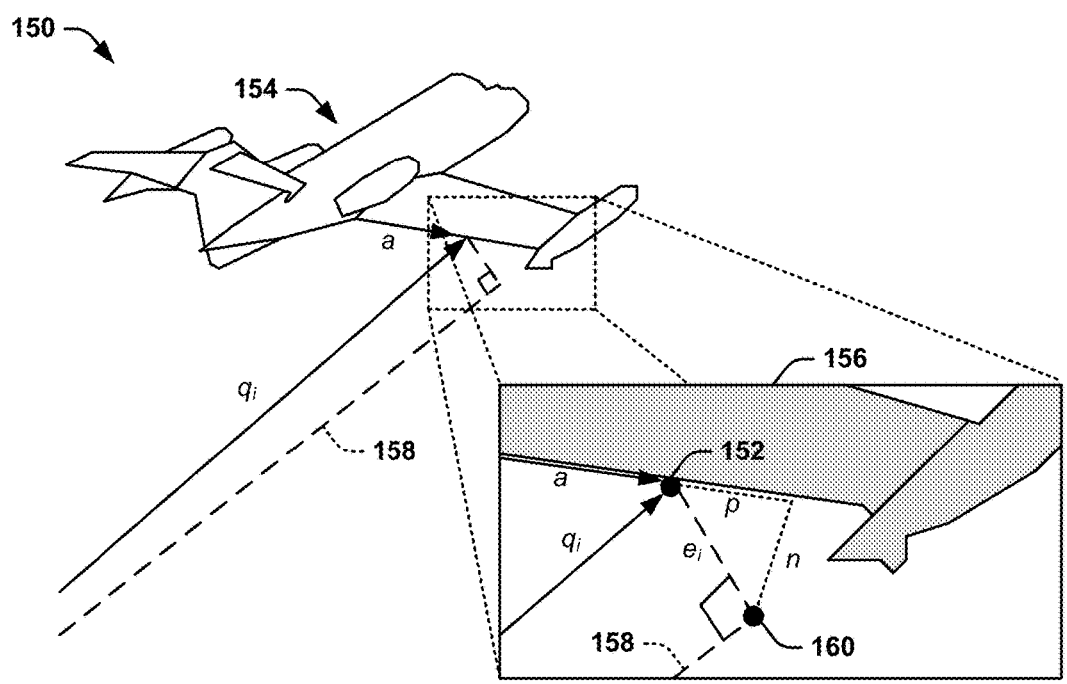
FIG. 4 illustrates another example diagram of pose-estimation relative to an image plane.

FIG. 4 illustrates another example diagram 150 of pose-estimation relative to a camera frame (not shown), which can correspond to the camera frame (X', Y', Z') in the diagram 100. Therefore reference is to be made to the example of FIGS. 1-3 in the following description of the example of FIG. 4. In the example of FIG. 4, a feature point 152 is demonstrated on the wing of an aircraft 154, and is demonstrated in an exploded view 156.

The diagram 150 includes a first vector $q_i$ that corresponds to a vector from a focal point to the feature point 152. The feature point 152 can correspond to an actual feature point 152 in three-dimensional space. The diagram 150 also demonstrates a vector 158 from the focal point to a perceived feature point 160, as perceived by the respective image sensor (e.g., one of the first and second cameras 56 and 58). Thus, the diagram 150 further demonstrates an error vector $e_i$ between the vector $q_i$ and the vector 158 corresponding to a difference in three-dimensional space between the actual feature point 152 and the perceived feature point 160 corresponding to the perceived location of the actual feature point 152. However, as described herein, the feature point 152 can correspond to one of a set of collinear feature points corresponding to a linear extension of the feature, such that the pose-estimation algorithm can analyze the collinear data set to calculate the error vector $e_i$ as an orthogonal offset extending along the collinear data set that includes the feature point 152 in an orthogonal direction.

As an example, with a lack of features providing depth perception of the aircraft 154 with respect to the cameras 56 and 58, the pose-estimate can rely on the reduction of object-space collinearity errors observed using features located close to one another with respect to the feature database. For groups of features which are collinear within the object reference space, the pose-estimate algorithm can identify these features with respect to a two-dimensional line referenced in the image space. The pose-estimation algorithm can thus process the feature points to identify features with little error normal to the two-dimensional line, but not necessarily parallel to it. In the example of FIG. 4, the collinear data set of feature points can extend along a linear extension corresponding to the wing of the aircraft 154. Thus, the trigonometric relationship of the feature points 152 and 160 is demonstrated by a vector p extending along the collinear data set of the feature points (e.g., along the wing) and a vector n corresponding to the normal extension of the error vector $e_i$ from the collinear data set of the feature points. Therefore, as described herein, the pose-estimation algorithm can iteratively minimize the error vector $e_i$ between the actual location of the feature in three-dimensional space and the perceived location of the feature based on consideration of the n component of the error vector $e_i$ alone (e.g., to mitigate collinearity error associated with the vector p).

In the examples of FIG. 4, to generate the pose-estimate, the pose-estimation algorithm evaluates the image data from both of the first and second cameras 56 and 58, similar to as described previously. The pose-estimation algorithm can implement reduction of normal errors, solely, for feature points that are identified by image processing with two-dimensional lines. For the collinear features, any errors that exist parallel to the collinear lines are ignored in the calculation of the pose-estimate. The normal error n in the example of FIG. 4, is defined as:

$$n = e - p_a e = e - \left(\frac{e \cdot a}{\|a\|^2}\right)a \qquad \text{Equation 22}$$

Where a is a predetermined unit vector input parameter to the pose-estimation algorithm defining a line of feature point collinearity. The quantity $\|a\|$ reduces to one because a is a unit vector. Therefore, Equation 22 replaces the calculation of the error $e_i$, as provided in Equation 4, with the error vector n. Given the normal error n, Equation 7 can be redefined as:

$$\sum_{i=1}^{n} \|e_i\|^2 = \sum_{i \in A,B} \|(I - \hat{V}_i)(R_c^T \cdot R_1 \cdot p_i + R_c^T \cdot t_1 + R_c^T \cdot t_c) - \qquad \text{Equation 23}$$
$$[(I - \hat{V}_i)(R_c^T \cdot R_1 \cdot p_i + R_c^T \cdot t_1 + R_c^T \cdot t_c) \cdot a]a\|^2$$

In Equation 23, A is defined as the set of all feature points visible in the first camera 56 and B the set of all feature points visible in the second camera 58, and all other variables are defined as previously provided. For features which do not require the object-space defined unit vector, and thus for the collinear feature set vector, a zero vector is passed in its place to reduce the function as follows:

$$\sum_{i \in A,B} \|\underbrace{(I - a_i a_i^T)(I - \hat{V}_i)(R_c^T)(R_1 \cdot p_i + t_c)}_{-b_i} + \qquad \text{Equation 24}$$

$$\underbrace{(I - a_i a_i^T)(I - \hat{V}_i)(R_c^T) \cdot t_1}_{A_i}\|$$

Following the same procedure outlined in the formulation of Equation 13, the optimum value of the translation vector $t_1$ is obtained as:

$$t_1 = \left(\sum_i A_i^T A_i\right)^{-1} \cdot \left(\sum_i A_i^T b_i\right) \qquad \text{Equation 25}$$

Where:

$$\sum_i A_i^T A_i = \sum_i (R_c)(I - \hat{V}_i)^T (I - a_i a_i^T)(I - \hat{V}_i)(R_c^T) \qquad \text{Equation 26}$$

$$\sum_i A_i^T b_i = \sum_i R_c \cdot (I - \hat{V}_i)^T (a_i a_i^T - I)(I - \hat{V}_i)(R_c^T)(R_1 \cdot p_i + t_c) \qquad \text{Equation 27}$$

The pose-estimation algorithm thus proceeds as described previously to determine the optimal rotation associated with the computed translation vector $t_1$. Accordingly, the pose-estimation algorithm can be simplified for more efficient generation of the pose-estimate for collinear feature point sets.

Figure 5:
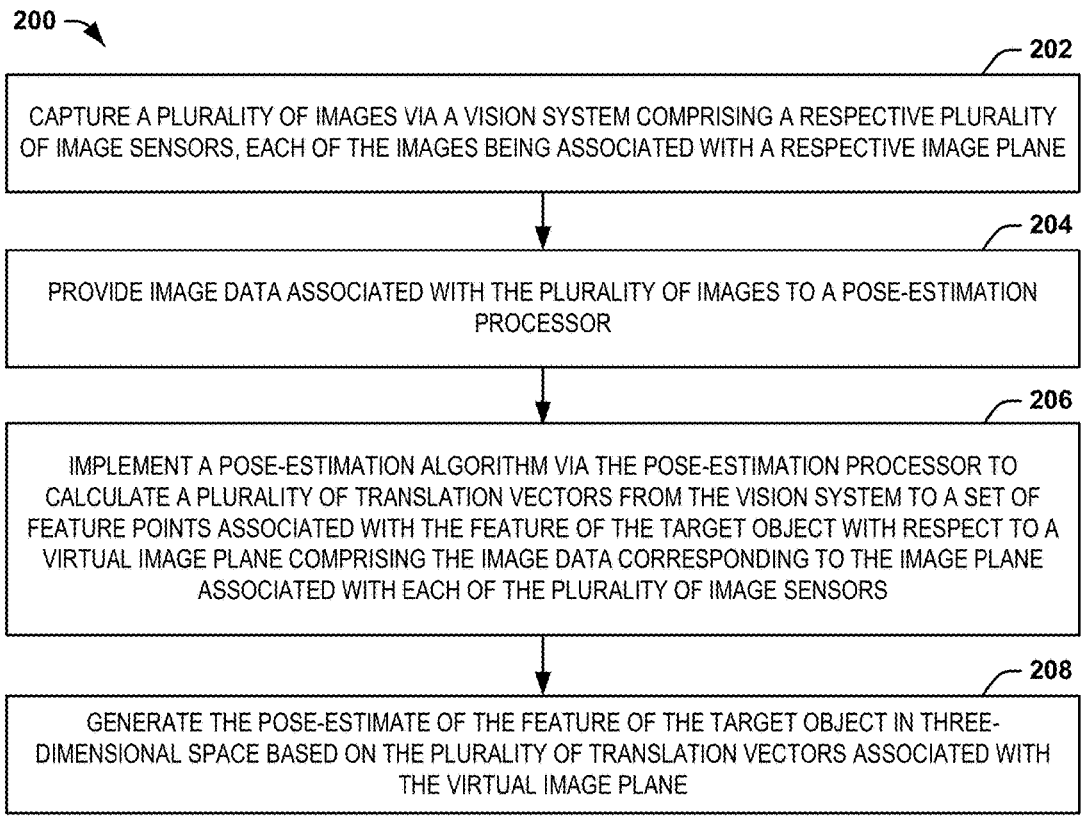
FIG. 5 illustrates an example of a method for generating a pose-estimate of a feature of a target object.

In view of the foregoing structural and functional features described above, a methodology in accordance with various aspects of the present invention will be better appreciated with reference to FIG. 5. While, for purposes of simplicity of explanation, the methodology of FIG. 5 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 5 illustrates an example of a method 200 for generating a pose-estimate of a feature (e.g., the feature 14) of a target object (e.g., the target object 12). At 202, a plurality of images are captured via a vision system (e.g., the vision system 16) comprising a respective plurality of image sensors (e.g., the image sensors 18). Each of the images can be associated with a respective image plane (e.g., the image planes 60 and 62). The image associated with at least one of a respective one of the plurality of image sensors can include the feature of the target object. At 204, image data (e.g., the image data IMG) associated with the plurality of images is provided to a pose-estimation processor (e.g., the pose-estimation processor 20). At 206, a pose-estimation algorithm is implemented via the pose-estimation processor to calculate a plurality of translation vectors (e.g., the translation vectors $q_i$) from the vision system to a set of feature points associated with the feature of the target object with respect to a virtual image plane comprising the image data corresponding to the image plane associated with each of the plurality of image sensors. At 208, the pose-estimate of the feature of the target object is generated in three-dimensional space based on the plurality of translation vectors associated with the virtual image plane.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A pose-estimate system comprising:
    a vision system comprising a plurality of image sensors, each of the plurality of image sensors captures an image with respect to a respective image plane, at least one of the respective images comprising a feature of a target object; and
    a pose-estimation processor aggregates the images corresponding to the respective image planes onto a virtual image plane to generate a pose estimate of the feature of the target object in three-dimensional space,
    wherein the pose-estimation processor is configured to implement a pose-estimation algorithm configured to calculate an error vector between an actual location of the feature in three-dimensional space and a perceived location of the feature in three-dimensional space with respect to a focal point of each respective one of the plurality of image sensors, and
    wherein the pose-estimation algorithm is configured to implement a least squares summation function to iteratively minimize the error vector between the actual location of the feature in three-dimensional space and the perceived location of the feature.

2. The system of claim 1, wherein the image plane associated with each of the plurality of image sensors is at least partially non-overlapping with respect to the image plane of each other one of the plurality of image sensors.

3. The system of claim 1, wherein the plurality of image sensors comprises a first image sensor that is configured to capture a first image with respect to a first image plane, wherein the pose-estimation processor is configured to implement a pose-estimation algorithm to spatially incorporate the image plane associated with each other one of the plurality of image sensors into the first image plane to generate the virtual image plane.

4. The system of claim 1, wherein the pose-estimation processor is configured to aggregate the images corresponding to the image plane associated with each of the plurality of image sensors onto the virtual image plane based on predetermined baseline spatial and orientation data associated with each of the plurality of image sensors with respect to each other.

5. The system of claim 1, wherein the pose-estimation algorithm is configured to evaluate N least squares summation function equation sets, where N corresponds to a quantity of the plurality of image sensors, such that the pose-estimation algorithm is configured to evaluate a set of feature points associated with a given one of the plurality of image sensors relative to a set of feature points associated with another one of the plurality of image sensors for each of the least squares summation function equation sets.

6. The system of claim 5, wherein the pose-estimation algorithm is configured to calculate a plurality of translation vectors from the vision system to a set of feature points associated with the feature of the target object with respect to the virtual image plane.

7. The system of claim 1, wherein the pose-estimation algorithm is configured to analyze a collinear data set corresponding to a linear extension of the feature and to calculate the error vector as an orthogonal offset extending along the collinear data set in an orthogonal direction.

8. The system of claim 7, wherein the pose-estimation algorithm is configured to implement a least squares summation function to iteratively minimize the error vector between the actual location of the feature in three-dimensional space and the perceived location of the feature, wherein the least squares summation function is configured to mitigate a collinearity error that is associated with error vectors that extend along the collinear data path in the least squares summation function.

9. A non-transitory computer readable medium that is configured, when executed, to implement a method for generating a pose-estimate of a feature of a target object, the method comprising:
    capturing a plurality of images via a vision system comprising a respective plurality of image sensors, each of the images being associated with a respective image plane, the image associated with at least one of a respective one of the plurality of image sensors comprising the feature of the target object;
    providing image data associated with the plurality of images to a pose-estimation processor;
    implementing a pose-estimation algorithm via the pose-estimation processor to calculate a plurality of translation vectors from the vision system to a set of feature points associated with the feature of the target object with respect to a virtual image plane comprising the image data corresponding to the image plane associated with each of the plurality of image sensors; and
    generating the pose-estimate of the feature of the target object in three-dimensional space based on the plurality of translation vectors associated with the virtual image plane,
    wherein implementing the pose-estimation algorithm comprises calculating an error vector between an actual location of the feature in three-dimensional space and a perceived location of the feature in three-dimensional space with respect to a focal point of each respective one of the plurality of image sensors, and
    wherein implementing the pose-estimation algorithm comprises implementing a least squares summation function to iteratively minimize the error vector between the actual location of the feature in three-dimensional space and the perceived location of the feature to evaluate a set of feature points associated with a given one of the plurality of image sensors relative to a set of feature points associated with another one of the plurality of image sensors.

10. The method of claim 9, wherein capturing the plurality of images comprises capturing the plurality of images via the respective plurality of image sensors in which the image planes associated with the respective plurality of image sensors are at least partially non-overlapping with respect to each other.

11. The method of claim 9, wherein the plurality of image sensors comprises a first image sensor that is configured to capture a first image with respect to a first image plane, wherein implementing the pose-estimation algorithm comprises spatially incorporating the image plane associated with each other one of the plurality of image sensors into the first image plane to generate the virtual image plane.

12. The method of claim 9, wherein implementing the pose-estimation algorithm comprises implementing analyzing a collinear data set corresponding to a linear extension of the feature and to calculate the error vector as an orthogonal offset extending along the collinear data set in an orthogonal direction to mitigate a collinearity error that is associated with error vectors that extend along the collinear data path in the least squares summation function.

13. A pose-estimate system comprising:
   a vision system comprising a plurality of image sensors, each of the plurality of image sensors captures an image with respect to a respective image plane, at least one of the respective images comprising a feature of a target object, the image planes being at least partially non-overlapping with respect to each other; and
   a pose-estimation processor that implements a pose-estimation algorithm to aggregate the images corresponding to the respective image planes onto a virtual image plane based on predetermined baseline spatial and orientation data associated with each of the plurality of image sensors with respect to each other, to calculate a plurality of translation vectors from the vision system to a set of feature points associated with the feature of the target object with respect to the virtual image plane, and to generate a pose estimate of the feature of the target object in three-dimensional space based on the plurality of translation vectors,
   wherein the pose-estimation algorithm is configured to calculate an error vector between an actual location of the feature in three-dimensional space and a perceived location of the feature in three-dimensional space with respect to a focal point of each respective one of the plurality of image sensors, and to iteratively minimize the error vector between the actual location of the feature in three-dimensional space and the perceived location of the feature based on a least squares summation function.

14. The system of claim 13, wherein the pose-estimation algorithm is configured to evaluate N least squares summation function equation sets, where N corresponds to a quantity of the plurality of image sensors, such that the pose-estimation algorithm is configured to evaluate a set of feature points associated with a given one of the plurality of image sensors relative to a set of feature points associated with another one of the plurality of image sensors for each of the least squares summation function equation sets.

15. The system of claim 13, wherein the pose-estimation algorithm is configured to analyze a collinear data set corresponding to a linear extension of the feature and to calculate the error vector as an orthogonal offset extending along the collinear data set in an orthogonal direction, and to iteratively minimize the error vector between the actual location of the feature in three-dimensional space and the perceived location of the feature, wherein the least squares summation function is configured to mitigate a collinearity error that is associated with error vectors that extend along the collinear data path in the least squares summation function.

* * * * *